United States Patent [19]
Darling et al.

[11] Patent Number: 5,591,462
[45] Date of Patent: Jan. 7, 1997

[54] BOTTLE INSPECTION ALONG MOLDER TRANSPORT PATH

[75] Inventors: Donald T. Darling, Palm Beach Gardens; Trent G. Francis; Brad L. Williams, both of Boynton Beach; Harold L. Dewar, Indialantic; David B. Delater, Stuart; Daniel B. Gold, West Palm Beach; Jerry Pentel, Tequesta, all of Fla.; Paul L. Wright, Marrieta, Ga.; Peter J. Sands, Leeds; Phillip Cochran, Bessemen, both of Ala.

[73] Assignee: Pressco Technology, Inc., Solon, Ohio

[21] Appl. No.: 343,015

[22] Filed: Nov. 21, 1994

[51] Int. Cl.⁶ .................................................. B29C 49/78
[52] U.S. Cl. ................. 425/173; 65/158; 250/223 B; 348/127; 356/240; 425/525; 425/534
[58] Field of Search ........................... 425/140, 169, 425/522, 534, 525, 162, 165, 173; 356/240, 237; 250/223 B; 348/127; 209/526, 524; 65/158, 165, 264, 267, 377

[56] References Cited

U.S. PATENT DOCUMENTS

| | | | |
|---|---|---|---|
| 3,880,750 | 4/1975 | Butler et al. | 209/526 |
| 3,932,042 | 1/1976 | Faani et al. | 356/240 |
| 4,214,860 | 7/1980 | Kleimenhagen et al. | 425/534 X |
| 4,280,624 | 7/1981 | Ford | 209/524 |
| 4,376,951 | 3/1983 | Miyazawa | 348/127 |
| 4,459,023 | 7/1984 | Reich et al. | 356/237 |
| 4,470,796 | 9/1984 | Stroup et al. | 425/534 X |
| 4,693,375 | 9/1987 | Schweers | 425/534 X |
| 4,790,741 | 12/1988 | Takakusaki et al. | 425/534 X |
| 4,850,850 | 7/1989 | Takakusaki et al. | 425/534 X |
| 4,914,289 | 4/1990 | Nguyen et al. | 250/223 B |
| 5,139,406 | 8/1992 | Hoshino et al. | 425/140 |

*Primary Examiner*—Richard L. Chiesa
*Attorney, Agent, or Firm*—Eckert Seamans Cherin & Mellott

[57] ABSTRACT

Camera based inspection equipment is used in conjunction with a multiple-station forming device such as a blow molder for polyethylene terephthalate (PET) or PEN bottle manufacturing. The inspection system relies on handling devices that present successive bottles for imaging, and due to their operation with the forming device it is possible to correlate inspection data with individual forming elements and/or transfer elements. A seal surface inspection module, a base/neck fold inspection module and a finish gauge inspection module are integrated into the route of preforms and containers through the container manufacturing equipment such that the inspection system is directed to view the passing bottles as they are carried on the transfer devices needed to load and unload the molder. The base/neck fold examines the lower portion of the bottles in elevation and plan view at the predetermined angle of orientation of the bottles on their longitudinal axes, maintained from the mold cavity to the inspection system, for examining the folds in the bottoms of the bottles. The seal surface module examines the surface to be sealed against a cap, in an axial inspection view. The finish gauge inspection module examines the threads and flanged neck.

32 Claims, 12 Drawing Sheets

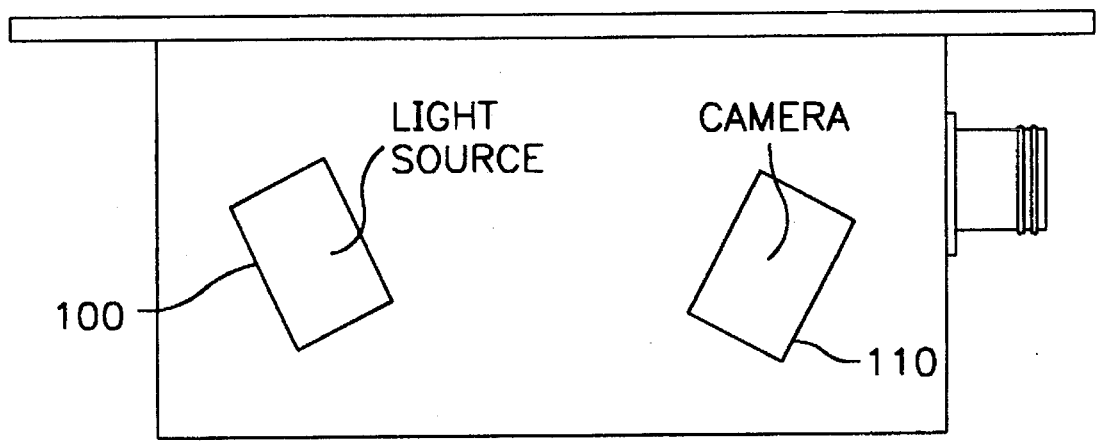
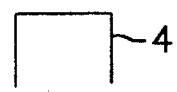
FIG. 3

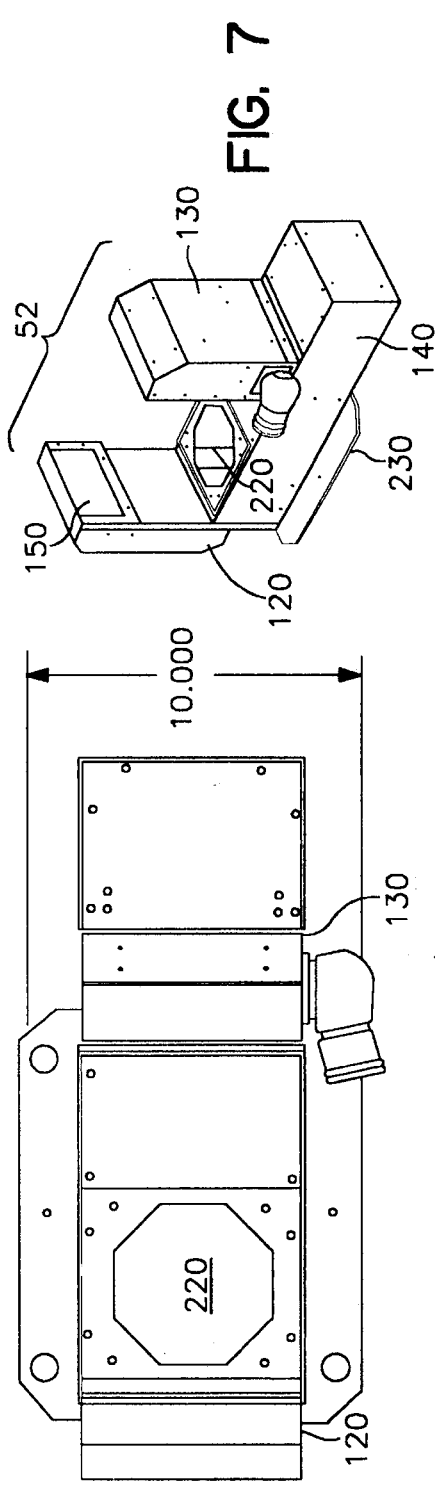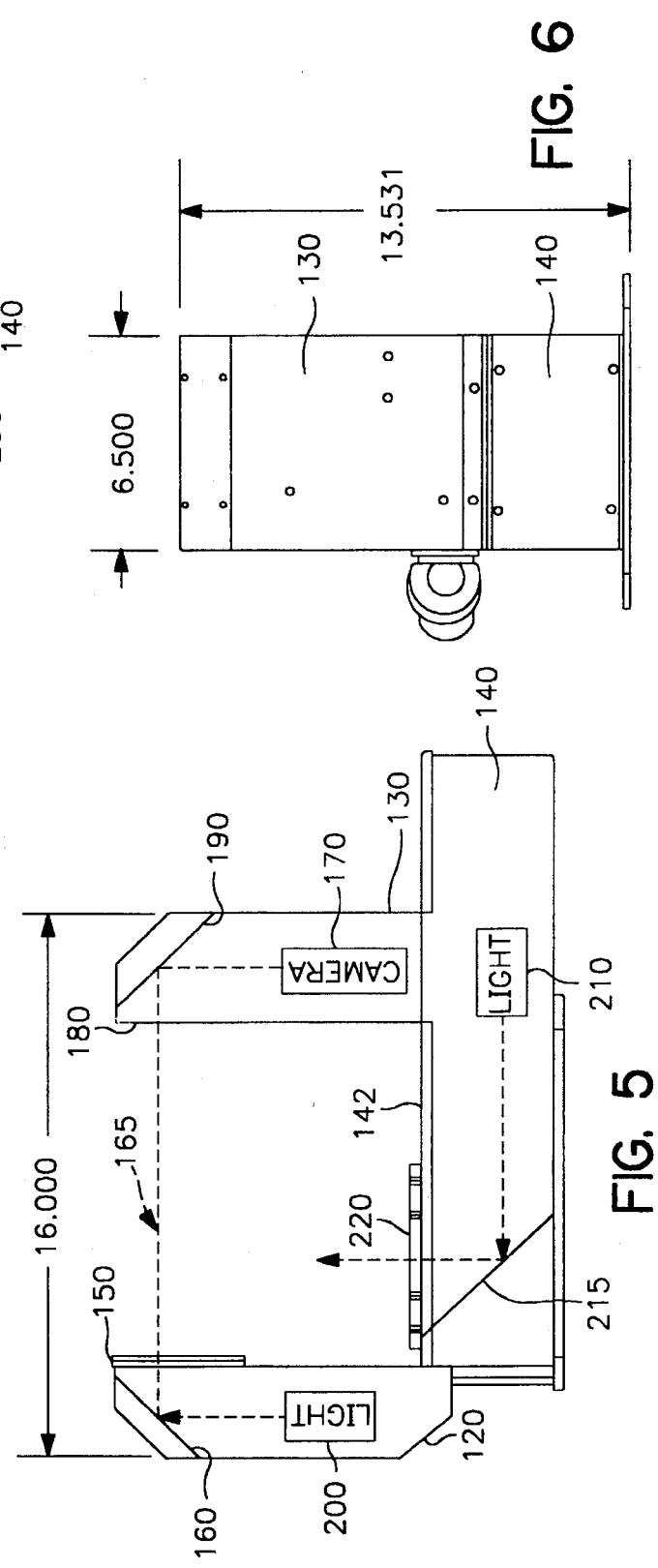

BOTTLE INSPECTION ALONG MOLDER TRANSPORT PATH

BACKGROUND OF THE INVENTION

1. Field of the Invention

The invention relates to the field of automated inspection equipment, and in particular concerns video based inspection equipment integrated with the manufacture of blow molded containers, especially containers of polyethylene terephthalate (PET), PEN or similar materials. The inspection system is fit into and synchronized with a multiple-station production machine, such that selections can be correlated to particular forming and conveying apparatus, and there is no interference by the inspection system with handling of the containers through production.

2. Prior Art

Automated optical inspection systems for containers such as beverage bottles are known and can be applied to the detection of defects in newly manufactured containers or used containers, e.g., containers that are recycled after being returned for deposit. Recycled bottles are cleaned and inspected for dirt or damage prior to refilling. U.S. Pat. No. 4,459,023-Reich et al. is an example of an inspection system for returnable bottles.

Returnable bottles are typically made of glass, whereas recycled plastic bottles are more likely to be comminuted and used as a source of plastic for other uses. Examples of defects that may render a returned glass bottle unusable are chips or cracks, especially associated with the surface to be sealed against a closure cap, cracks, dirt and extensive scuffing of the exterior surface.

Newly manufactured bottles are less likely to have comparable defects because they have not yet suffered rough handling during distribution or consumer use. However, new containers also can be inspected for defects that may arise due to the manufacturing process used to make them. One such process involves the blow-molding of polyethylene terephthalate containers, which are in use for beverage containers and the like.

In a typical inspection system, for example for returnable bottles, the inspection system treats each bottle independently of all other bottles. Bottles which are rejected are diverted from the serial stream of bottles, typically by a reject mechanism located some distance downstream from the inspection system along a conveying means. This requires a shift register or other synchronizing means causing the downstream diverter to operate on the correct bottle when it arrives. Since there is no relationship between the bottles being conveyed and inspected, data from the inspection system can only be used to develop statistical information respecting the overall population of bottles.

In a production setting, information collected at inspection stations and other quality assurance steps is advantageously correlated to the particular materials, apparatus and the like that were used to produce the product being checked. Process engineers therefore may attempt to cross-correlate selections rates with the content of specific batches of material, process parameters such as temperatures and pressures measured during production, etc., in order to adjust the process parameters so as to maximize selections.

According to the present invention, an inspection system is integrated with and synchronized to a multiple station production machine wherein each of the stations is used repetitively in turn. As a result, it is possible separately to analyze the performance of each station. Unlike container inspection systems that treat each container independently, the system of the invention is useful for correlating selection information to elements of the production machine. This is especially useful in the blow molding of PET/PEN bottles.

PET/PEN material is durable and light in weight. The manufacturing process typically involves preliminary molding of the closure end of the container, retaining a preform that is then heated to softening and blow molded to form the container body. The container body can have a flat bottom that may be covered by a plastic cup for protecting the bottom and making the empty container bottom-heavy. According to another technique, the bottom of the container is formed into folds that define lobes for strengthening the bottom. An example is the so-called "petaloid" bottom configuration, having several lobes formed by folds in the bottom of the container during the molding process.

Whether used for new containers or containers returned for re-use, the typical bottle inspection system is a stand-alone unit mounted along a conveyor. The containers successively pass through an inspection station where optical apparatus record one or more images of the container by one means or another, and analyze the data for defects. Such defects typically are detected from unexpected variation in the reflectance level of the bottle or its light transmission characteristics, wherein a local variation in reflectance or transmissiveness may be due to a crack, chip or molding fault.

An example of such a stand alone bottle inspection system may be seen in U.S. Pat. No. 3,932,042-Faani et al., which discloses an inspection system which utilizes a conveyor to transport a line of newly manufactured bottles through an inspection station. The inspection station performs various optical tests on each of the bottles in the line. The inspection system triggers a deflection mechanism or kicker downstream along the conveyor, and either accepts or rejects each bottle based on the test results. The reject signal can operate a solenoid, air cylinder or the like to remove or divert a rejected bottle.

The optical tests used to detect defects can be complicated or simple, and various optical inspection techniques can be used to resolve the different defects that can occur. A simple test could involve, for example, checking only for a correctly shaped sealing surface on the end of the bottle, or only for gross defects in the external contour. While these are useful tests, it would be advantageous to provide a sequence of tests for a variety of potential defects. Thus the sidewalls of the bottle can be examined, neck threads can be checked for continuity, the endmost sealing surface can be checked for smoothness and the bottom lobes can be checked for complete formation during molding.

It has been found according to the present invention that certain defects caused by physical obstructions in particular mold cavities or blow molding conduits can persist through successive uses of the cavities or the like. As a result, in a multiple station apparatus having N stations, every Nth container may have a similar defect. Similarly, a temperature or pressure problem at a given mold cavity may not cause a defect with every use, but may simply be statistically more likely to cause a defect. Furthermore, certain kinds of different defects can be related to the same deficiency of the molding apparatus. Using a digital processor in sync with the molding equipment according to the invention, it is possible to identify problems more quickly and to use the synchronous relationship of the inspection and molding steps to isolate the exact cause of molding problems. The same is true of problems in handling equipment synchronized to the molder, such as damaged grasping apparatus.

In Faani et al., an inspection system illuminates each bottle from two different directions as the bottle is transported along a conveyor. The light passes through or is reflected by various portions of the container and is directed through a mirror arrangement and resolved to form an image. The image is presented to a single scanning device such that the scanning device attempts to glean enough information to accept or reject the bottle without its having to be rotated for presentation of all the sides.

U.S. Pat. No. 3,880,750-Butler et al. discloses an inspection system for inspection of the sealing surface of the bottle, namely the endmost surface that forms a sealing closure together with a cap. A light source is positioned above the rim of the bottle and directs an intense spot light of light onto the rim. A detector is positioned above the rim of the bottle such that light reflected from the rim is passed through a mask to a detector. The bottle under inspection is rotated about its vertical axis during the inspection cycle, and variations in the detected light level are detected when caused by scattering of the light beam by a defect. The electronic signal produced by the detector can be processed through circuitry allowing the system to detect several types of defects in the shape or character of the sealing surface.

The foregoing inspection systems are ancillary to the container production steps because the inspection system can be placed at any point where there is a stream of containers moving along a conveyor and synchronism of the inspection and production are not required. This is advantageous for an inspection system because the inspection system needs a clear view of the containers, free of obstruction by handling equipment, conveyor rails and other structures that could conceal a defect. The inspection station can have distinct handling apparatus specifically adapted for inspection steps. For example, the handling apparatus may be designed to engage and rotate each bottle during the inspection cycle to ensure that each sidewall is presented for inspection. On the other hand, the mechanism associated with an inspection step such as rotating the bottle, may be inconsistent with another step, such as examining the sealing surface or threads. Therefore, a comprehensive inspection system tends to be relatively complex.

It would be desirable to integrate an inspection system with container manufacturing equipment, so as to eliminate the need for additional handling equipment such as conveyers and other dedicated equipment. The present invention is intended to integrate inspection steps with manufacturing steps, especially in the blow molding of polyethylene terephthalate beverage containers and the like, for identifying and segregating defective containers as early as possible during their production and handling, and by inspecting the containers when the manufacturing equipment happens to orient the containers appropriately for certain inspection steps. Moreover, by integrating the inspection system closely with the container production equipment (e.g., the molder) and the feeding and take-out apparatus that are synchronous with the production equipment already, the foregoing capability of correlating selection results and even specific types of defects, to the particular station that produced each container, is greatly enhanced.

SUMMARY OF THE INVENTION

It is an object of the invention to provide an inspection system for containers and the like, which is closely integrated to manufacturing equipment that produces the containers.

It is another object of the invention to provide an inspection system having discrete optical inspection heads located between certain components of the manufacturing equipment such that inspection steps are conducted when the containers are disposed appropriately for inspection, without the use of dedicated transport mechanisms.

It is another object of the invention to provide an inspection system which can inspect newly formed bottles utilizing the existing transport mechanisms which are required during the manufacture of bottles, and moreover which is synchronized to the transport and production mechanisms such that selection data can be correlated thereto.

It is another object of the invention to provide an inspection system which provides 100% inspection of newly manufactured bottles as they are transported through the manufacturing equipment.

It is still another object to coordinate the operation of plural inspection heads, for collecting a relatively complete data record representing an inspected container, and to analyze the data and thereby discriminate for defective containers that are diverted by triggering of a downstream mechanism along the manufacturing line.

These and other objects are accomplished by a video inspection system used in conjunction with a plural-station forming and conveying apparatus such as a blow molder for polyethylene terephthalate PET or PEN container manufacturing, and other such forming apparatus including a number of production and/or handling stations. The inspection system is closely integrated with the production machine, and more particularly is placed where the handling equipment presents successive containers for imaging in required inspection areas. A seal surface inspection (SSI) module, a base/neck fold (BNF) inspection module and a finish gauge inspection (FGI) module are integrated into existing bottle manufacturing equipment such that the inspection system is directed to view the passing bottles. The base/neck fold examines the lower portion of the bottles in elevation and plan view at the predetermined angle of orientation of the bottles on their longitudinal axes, maintained from the mold cavity to the inspection system, for examining the folds in the bottoms of the bottles. The seal surface module examines the surface to be sealed against a cap, in an axial inspection view. The finish gauge inspection module examines the threads and flanged neck.

The inspection system has inspection heads arranged passively to encompass different points along a container manufacturing sequence. The seal surface inspection (SSI) module reflectively examines the endmost container sealing surface. The base/neck fold inspection module (BNF) forms a tunnel passage for viewing the lower portion of finished containers along and transverse to a longitudinal axis of the containers. The BNF module can be located where preforms and molded bottles pass one another at a nip point between a molder loading preforms transfer device and a molder unloading finished container transfer device, such that both the preforms and the containers move through the tunnel passage. The BNF module is synchronized to capture at least one view of the containers between two adjacent preforms. The finish gauge inspection module (FGI) inspects the threads and can be disposed on a starwheel exit conveyor. A processor coupled to the inspection devices and to sensors operable to synchronize inspection to the operation of the molder and transport devices, coordinates operation of the inspection heads and triggers the operation of a rejection mechanism for diverting containers found to be defective. Moreover, the processor can correlate the results of inspection with the particular plural stations, for monitoring separately the operation of individual mold cavities, transfer mechanisms and the like.

BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the scope of the appended claims. In the drawings.

FIG. 3 is a front view of the Seal Surface inspection module.

FIG. 4 is a top view showing the portion of a base/neck fold inspection module used for examining lower areas of the container in accordance with the invention.

FIG. 5 is a front view of the base/neck fold lower inspection module.

FIG. 6 is a side view of the base/neck fold lower inspection module.

FIG. 7 is an isometric view of the base/neck fold lower inspection module.

DETAILED DESCRIPTION OF THE PREFERRED EMBODIMENTS

Figure 1:
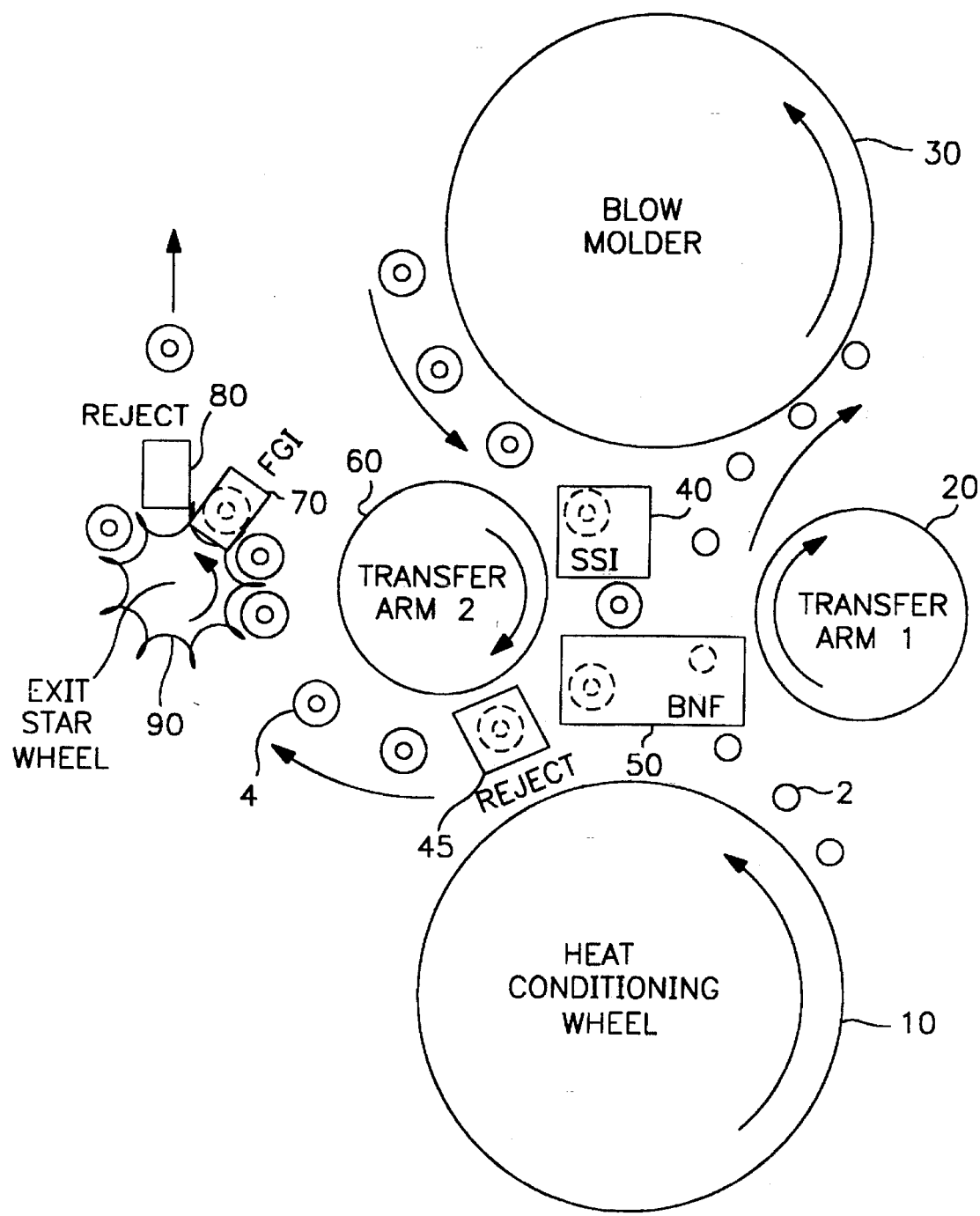
FIG. 1 is schematic view of the inspection system of the invention, integrated with a container manufacturing system having plural handling steps, specifically illustrated as container blow molding equipment.

Referring to FIG. 1, the inspection system is shown schematically integrated with an operative bottle manufacturing apparatus. Specifically the invention is shown integrated with a SIDEL® SBO 24/24 blow molding machine. This type of manufacturing apparatus is a "stretch blow-molder" type and is useful for the production of PET or PEN bottles. It will be apparent to those skilled in the art that the invention is also adaptable to other types and brands of bottle manufacturing equipment.

The manufacturing process begins with a pre-form 2, essentially comprising a partially formed PET/PEN (plastic) blank which is injection molded for forming a neck with a substantially depending but unexpanded body, and then blow molded for forming the body of the container, e.g., a beverage bottle or the like. The pre-form has a top seal surface, a threaded portion and support flange, which remain intact during the process of blow molding the body portion in one of a plurality of repetitively operated mold cavities in a carousel molding arrangement ted by a preform transfer device 20 and unloaded by a molded container transfer device 60. The lower portion of the pre-form that will become the container body is test-tube shaped and is composed of sufficient plastic material to be expanded to form the sidewalls and base of the bottle when the preform is heated to softening and pressurized within the vented mold cavity such that the container body expands into the desired shape.

The preforms are loaded onto heat conditioning wheel 10 which has a plurality of spindles operable to receive the preforms. The heat conditioning wheel moves the spindles passed a plurality of heating elements which heat the preform to a softening temperature in preparation for blow molding the body portion of the bottle. A first transfer arm 20 (the preform transfer device) removes the heated preforms and transfers them to the blow molder 30, i.e., to the next available cavity. The blow molder 30 is carousel shaped and has a plurality of bottle-shaped cavities (not shown), defined by surfaces that are cooled by chilled water or the like. One or more blow nozzles (not shown) are inserted and pressurize the internal volume of the softened pre-forms when disposed in the mold cavities. The cavities are shaped to define the external shape of finished bottles. The SIDEL® SBO 24/24 is operable to mold bottles from ¼ to 2 liters in volume.

The first transfer arm deposits the preform into one of the plurality of cavities. The blow nozzle is then engaged with the open top or neck of the heated preform and pressurized air is directed through the blow nozzle to inflate the pre-form in the cavity. The preform is inflated until the heated and softened plastic is distended into contact with the cooled walls of the cavity. The plastic cools rapidly and hardens, thereby forming a bottle 4 with a top seal surface, a threaded portion and support flange, a neck formed with an opening, a body and a base. The bottle can be formed with folds in the bottom, i.e., in the known petaloid shape.

The heat conditioning wheel 10, transfer arms 20, 60 and molder 30 all operate serially and synchronously, as necessary to pass the containers between them. Therefore, a reliable relationship exists between the bottles and the particular transfer station and molding station that the containers moved through. In addition, the rotational orientation of the bottle on its axis upon leaving the molding apparatus, most notably the orientation of the folds and other non-circular features, is a function of the orientation of the mold cavities. Whereas the procedure is repeated for all of the containers being produced, the containers are oriented at a known rotation angle upon passing out of the blow molder to the second transfer arm 60 (see FIG. 1), and are in a known sequence. The handling equipment necessarily retains the sequence, and preferably also the rotation angle, while the containers are engaged in a manner that allows the containers to be presented to the inspection apparatus.

For this purpose, each container is removed from the cavity by a second transfer arm 60 which transports the container to passed a first diverter mechanism (or reject arm) 45 which can controllably divert selected containers or allow the containers to be transferred to an exit star wheel 90. The exit star wheel 90 transports the container passed a second diverter mechanism (or reject arm) 80 which can controllably divert selected containers or allow them to pass to other means (not shown) where the containers may be processed further for packaging, etc.

A seal surface inspection (SSI) module 40 is coupled directly along the normal manufacturing path of the SIDEL® SBO 24/24 blow molding equipment. The seal surface inspection module is operable to illuminate and image the top seal surface of the bottle. This image is substantially an annular image (i.e., it is not dependent on the rotational angle of the container on its axis).

A base/neck fold (BNF) inspection module 50 is also coupled directly in the normal manufacturing path of the SIDEL® SBO 24/24 blow molding equipment, along a path from the blow mold cavity wherein the orientation of the containers remains known due to their being carried on the transfer arms. The base/neck fold inspection module 50 is operable to inspect the base of the bottle, and the neck area for various defects. Whereas the orientation of the containers is known, the BNF module can be oriented to view the containers at a predetermined orientation relative to the folds of the bottom, or perhaps to view at a plurality of known orientations.

A finish gauge inspection (FGI) module 70 is also coupled directly in the normal manufacturing path of the SIDEL® SBO 24/24 blow molding equipment. The finish gauge inspection module inspects the threaded portion of the bottle for various defects. The finish gauge inspection of the containers can include rotation of the containers on their axes, for viewing the threads around the neck. However, by this point the orientation of the bottom folds is no longer important because they have already been inspected.

Figure 13:
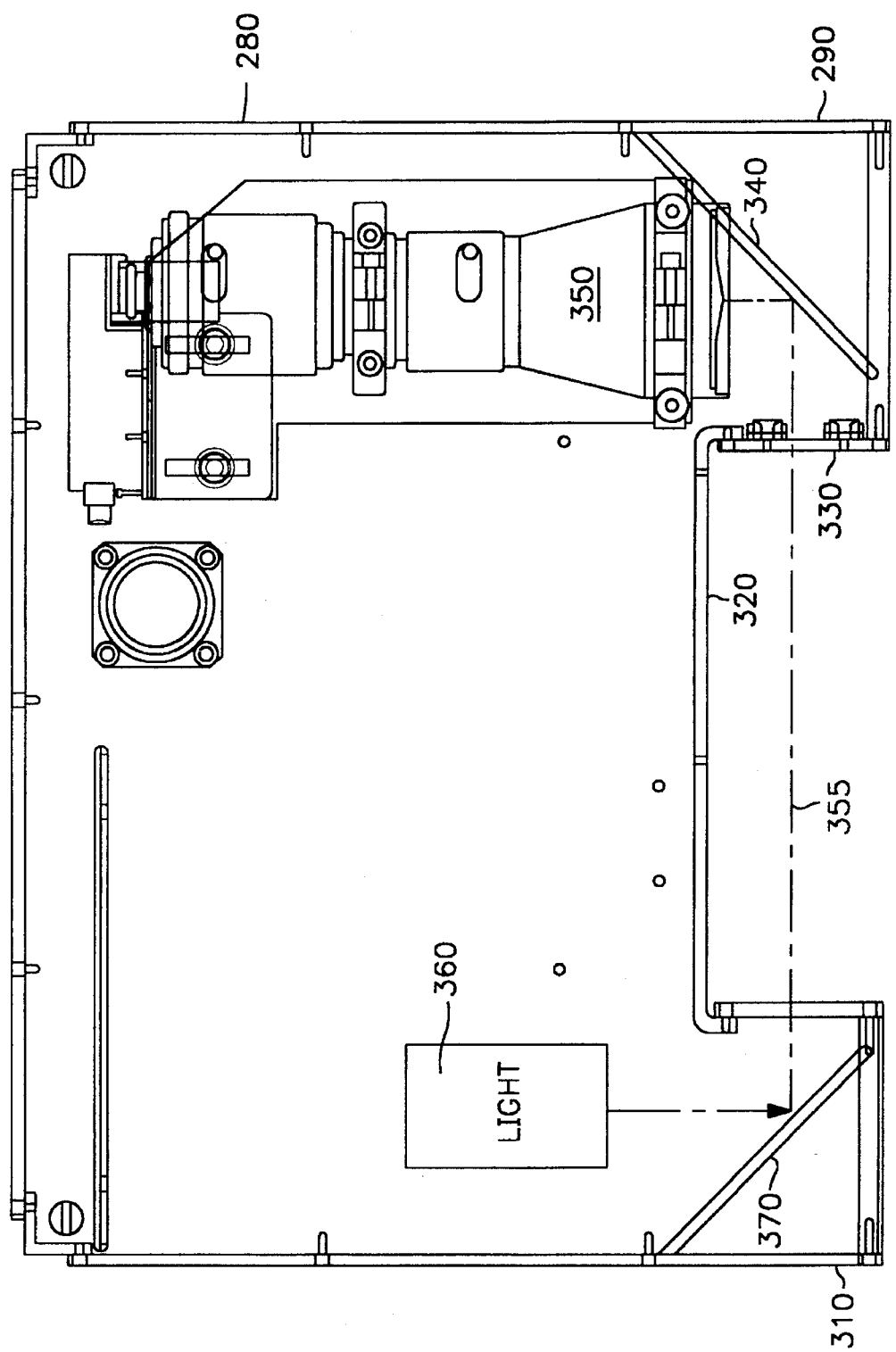
FIG. 13 is a front view of the Finish Gauge inspection module with its front cover removed.
Figure 14:
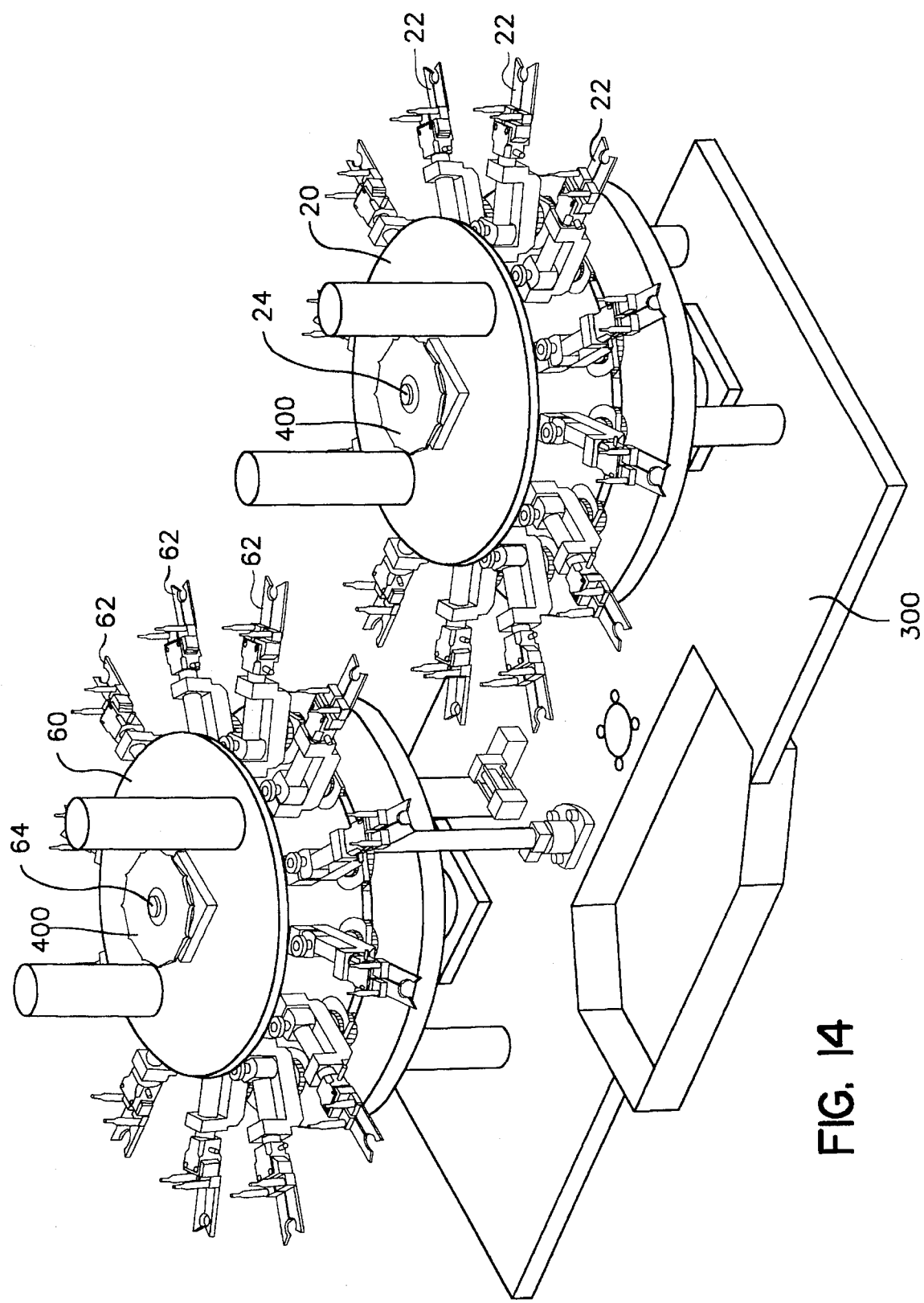
FIG. 14 is an isometric view showing first and second transfer arms arranged to move containers through production steps.
Figure 15:
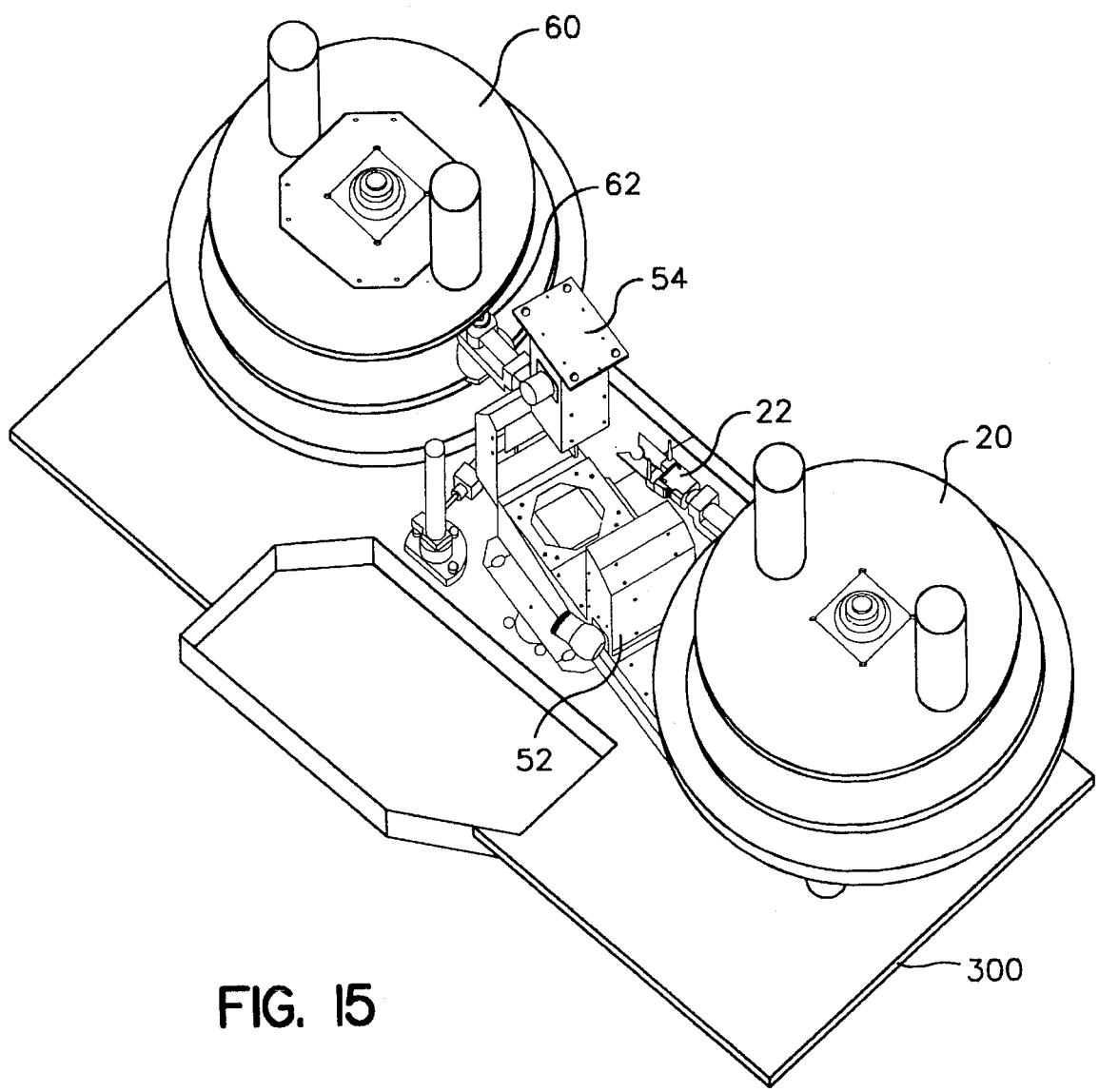
FIG. 15 is an isometric view of the first and second transfer arms with the base/neck fold inspection module installed according to the invention.
Figure 16:
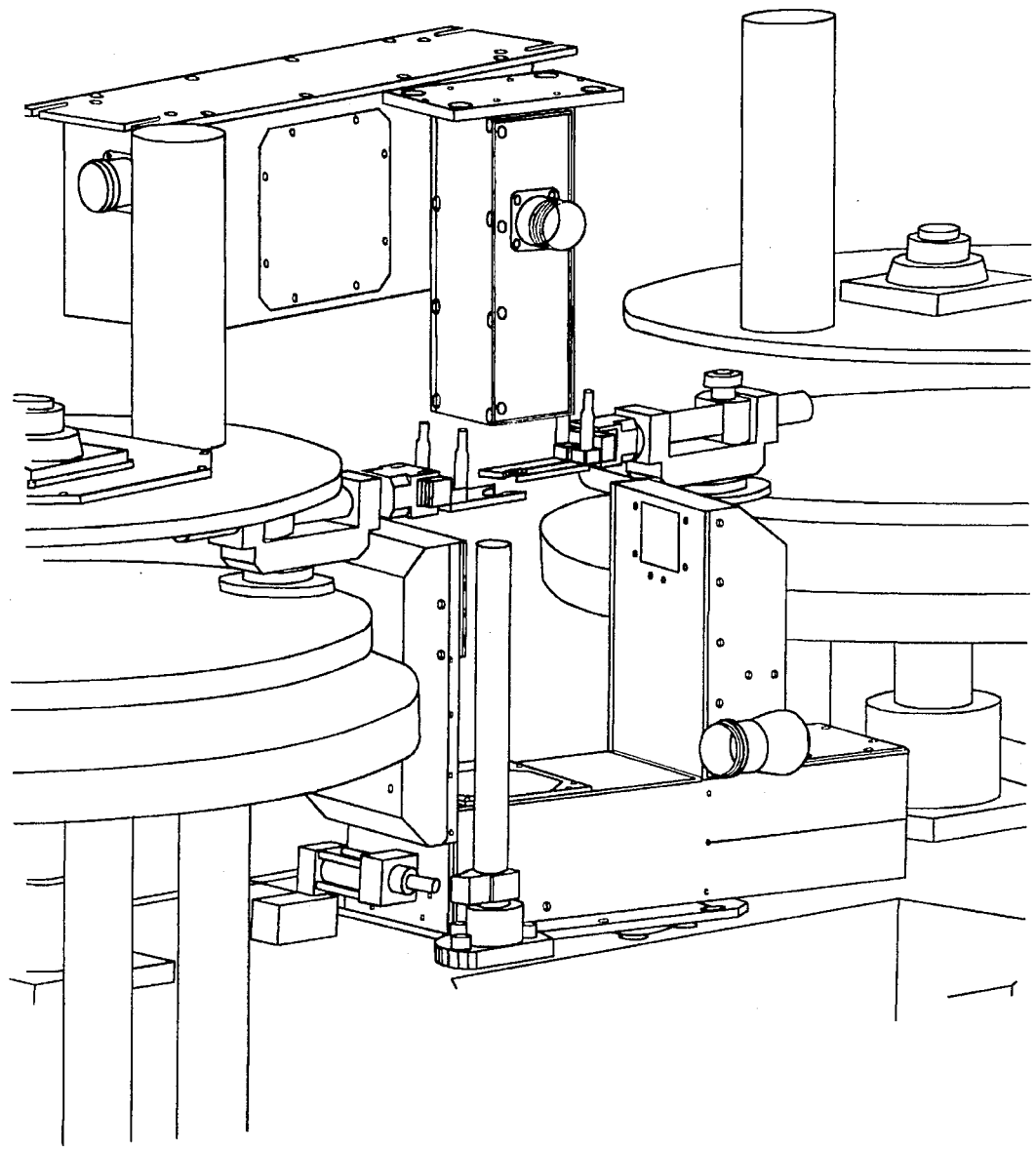
FIG. 16 is a partial isometric view of the first and second transfer arms with the base/neck fold and the Seal Surface inspection modules installed according to the invention.

FIGS. 2–13 illustrate particular arrangements for the respective inspection heads, and FIGS. 14 and 15 show the mechanical transfer arm structures that maintain the orientation of the containers.

Figure 2:
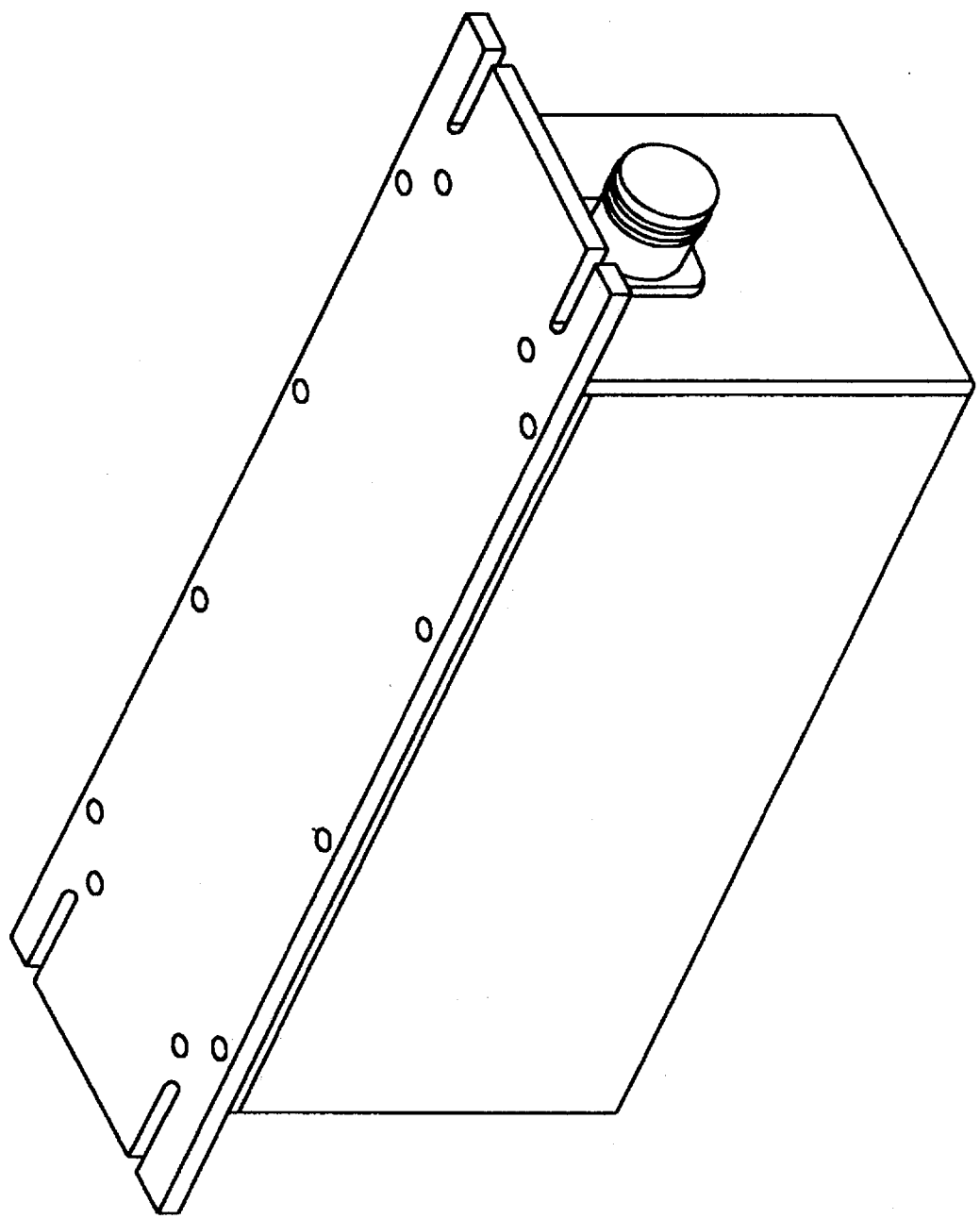
FIG. 2 is an isometric view showing a seal surface inspection module in accordance with the invention, adapted to examine a sealing end surface of containers being produced.
Figure 11:
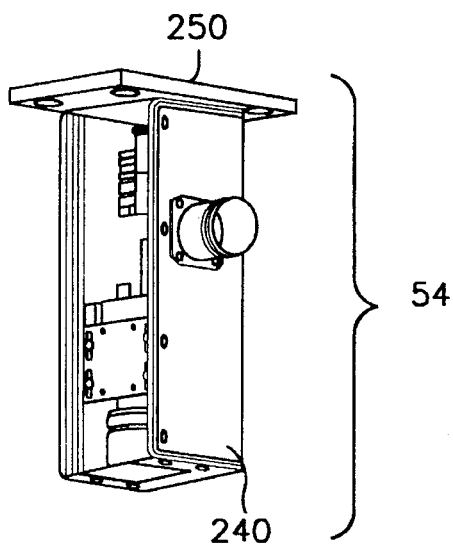
FIG. 11 is an isometric view of the base/neck fold upper inspection module.

As shown in FIGS. 2 and 3, the seal surface inspection (SSI) module has a light source 100 which directs light at an incidence angle toward the top seal surface of the bottle 4, which seal surface is preferably smooth and flat as needed to effect a complete seal with a cap (not shown) when the bottle is later filled. Camera 110 likewise is aimed at the top seal surface of the bottle, preferably opposite the light source and at the same relative angle. Camera 110 receives an image formed from the light reflected off of the top seal surface. Camera 110 can include a charge coupled device (CCD) array, suitable optics for focusing the image on the array, and a digitizer and controller for grabbing a frame, i.e., digitizing the image as an array of pixel data that can be analyzed for the expected image of a good seal surface.

A non-defective top sealing surface defines a smooth and unbroken annular ring. Reflected light from a non-defective top sealing surface is uniform in that the amplitude of reflected light is the same regardless of what portion of the top sealing surface is imaged. Defects in the top sealing surface cause the light from the light source 100 to be locally reflected or refracted, or otherwise scattered such that the camera 110 receives a rise or fall in the light amplitude as compared with a non-defective top sealing surface. In addition for testing for a smooth sealing surface (as indicated by a uniform annular ring image), the image can be measured for maximum/minimum diameter, out-of-round and the like as well.

Collection of an image by the SSI module preferably is triggered by a sensor ring having a plurality of capacitive proximity detectors which sense when the container is known to be in the proper position as indicated by the phase angle of the machine as a whole, as discussed below. Alternatively the SSI module can be triggered by a lamp/photocell pair (not shown) whose beam path is broken by the container or by the transfer arm. Alternatively, other angle encoding means such as limit switches or the like can synchronize image collection to the position of the transfer arm and the container therein.

The base/neck fold (BNF) inspection module 50 is disposed next along the path of the containers, at a position wherein the containers remain engaged by the transfer arms. BNF 50 has a lower module 52 (FIG. 7) and an upper module 54 (FIG. 11) that generally form a tunnel but allow clearance for the grasping mechanisms of the transfer arms 20, 60. The lower module is shown in FIGS. 4–7. The lower module is generally U-shaped and has a first and second leg 120, 130 which extend in the upward direction joined by a center yoke section 140. The lower module 52 also has a mounting plate 230 formed with a plurality of mounting holes, whereby the inspection module can be arranged to view containers passing along the path of the transfer arms. Generally, like the SSI module, the BNF module is arranged to view the containers without interfering with the passage of the containers along the path defined by the production apparatus.

FIG. 5 is a schematic representation of the internal construction of lower module 52 of BNF module 50. The first leg 120 has an opening, through which light can pass, covered by a first glass panel 150. The glass panel can be clear or difuse to provide even backlighting. A first mirror 160 and first light source 200 are positioned such that light from the first light source is reflected off of the first mirror 160 and passes through the first glass panel 150. First mirror 160 is set at a 45° so that reflected light travels along the line of sight 165 between the two legs 120, 130 as shown by dotted lines.

The second leg has an opening through which light can pass along line of sight 165 (see FIG. 5). A camera 170 is positioned to collect an image that is reflected off of a second mirror 190. The second mirror 190 is also set at a 45° so that the camera receives an image from the area between the two legs 120, 130 along the line of sight 165. The position of the line of sight is such that when a bottle is placed between the two legs, the line of sight passes through the upper area of the bottle adjacent the neck. The camera 170 receives an image representing the outline of the container and (for clear containers) a view through the sidewalls.

A second light source 210 is located in the center yoke section 140 and directs light at a third mirror 215. The third mirror is set at a 45° so that light is directed though an opening in the top panel 142 of the center yoke section. The opening in the center yoke section is likewise covered by a second glass panel 220, which can be clear or diffuse. Light from the second light source travels in the upward direction parallel to the two legs and passes into the material of the bottle. This light tends to illuminate features that are inclined at other angles than the features primarily illuminated along line of sight 165. In any event, the bottle provides an image that can be tested for contrast features in certain areas and compared against the standardized image of a "good" bottle as stored in memory or in the image analysis procedures effected on a frame grabbed by the camera.

In an alternate embodiment, the third mirror 215 is not used and the second light source is placed directly under the second glass panel 220 such that light travels in an upward direction parallel to the two legs and passes into the material of the bottle.

Figure 8:
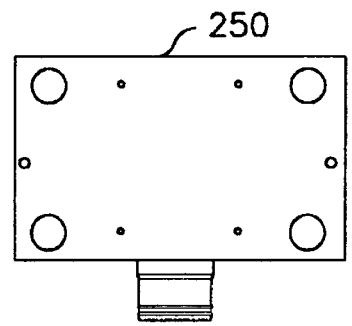
FIG. 8 is a top view of the base/neck fold upper inspection module in accordance with the invention.
Figure 9:
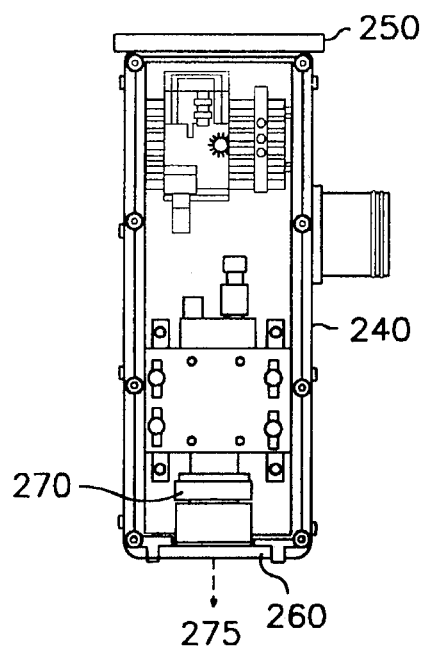
FIG. 9 is a front view of the base/neck fold upper inspection module.
Figure 10:
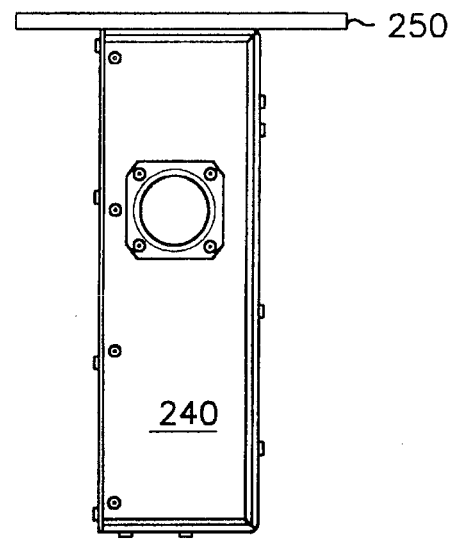
FIG. 10 is a side view of the base/neck fold upper inspection module.
Figure 12:
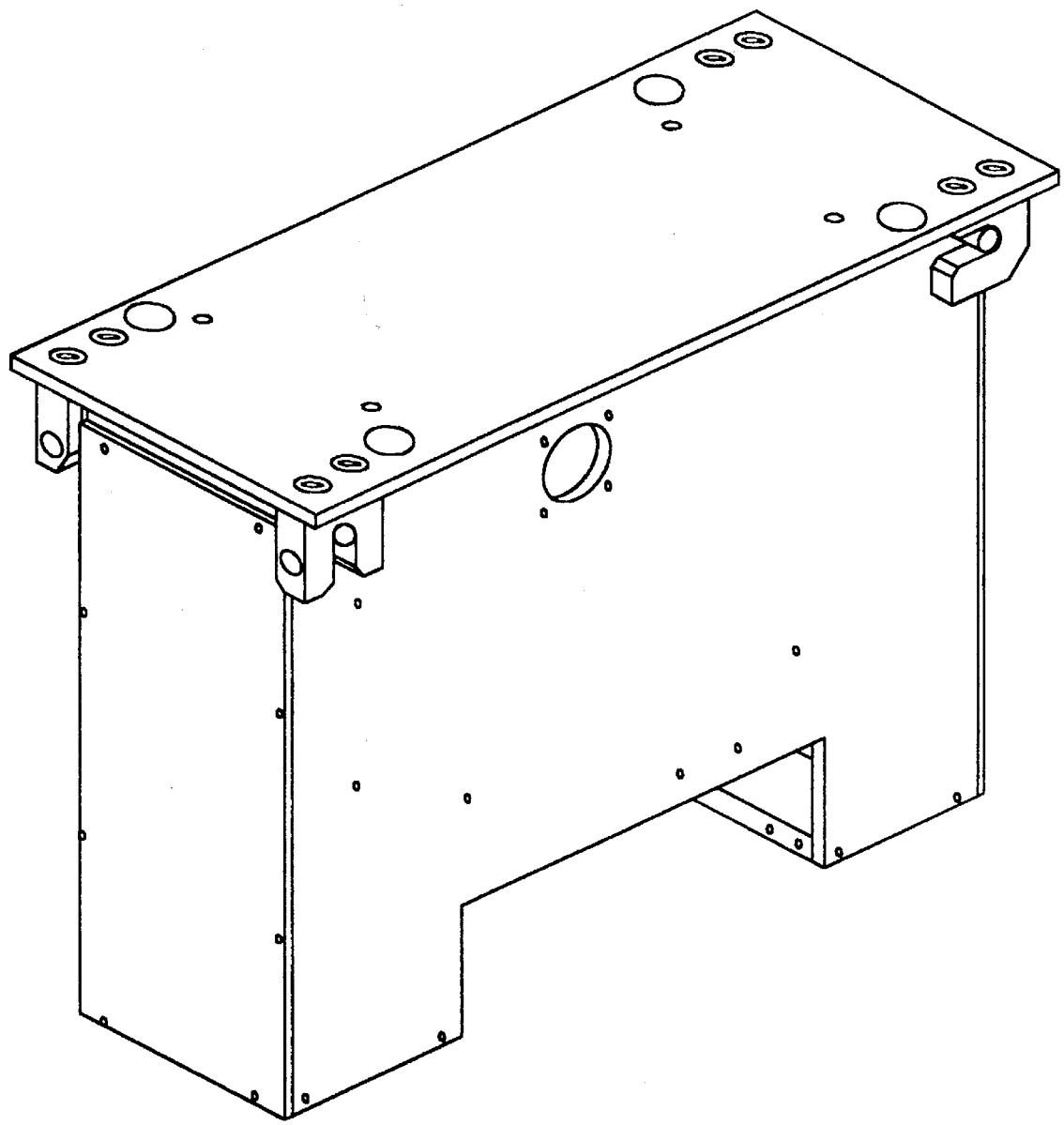
FIG. 12 is an isometric view of a finish gauge inspection module in accordance with the invention.

FIGS. 8–11 show a preferred embodiment of the upper module 54 of the BNF module 50. Upper module 54 has a generally rectangular body 240 and a mounting plate 250. FIG. 8 shows a view of the upper module with the front cover removed. The rectangular body has an opening at the bottom covered with a glass plate 260. A camera 270 is mounted inside the rectangular body such that the camera can receive images of objects directly below the upper module along the line of sight 275 shown by a dotted line in FIG. 9, and collects light passing upwardly from the lower module 52. Thus the upper module collects a plan view image of the bottle or other container, and as with the elevation image the plan view image can be analyzed and compared to various stored standards whereby "good" and "bad" bottles are discriminated from one another.

FIG. 15 shows the mounting relationship of the upper and lower modules 52, 54 with respect to a first and second transfer arm 20, 60. The first and second transfer arms are shown in simplified form with only a single arm member 22, 62 being shown attached to each. Referencing FIG. 14 it can be seen that the first and second transfer arms actually have a plurality of arm members 22, 62 at angularly spaced positions, such that successive containers move along an identical path through the inspection apparatus in a regular, evenly-spaced progression. The first and second transfer arms 20, 60 are coupled to axles 24, 64 respectively such that the transfer arms are operable to rotate about the axles.

Referring briefly to FIG. 1, first and second transfer arms 20, 60 are positioned such that preforms 2 and newly formed bottles 4 pass in close proximity and in a phased relationship. There is insufficient space to view the bottles alone along a radial line relative to transfer arm 60, because the molded bottles pass immediately adjacent the preforms. However, the two transfer arms 60, 20 necessarily maintain a stable phase relationship in that they both interface with molder 30. Accordingly, the first and second legs 120, 130 of BNF module 50 are spaced sufficiently to permit both the bottles and the preforms to pass between them. The BNF module is synchronized with respect to the position of a bottle (and therefore also the preform). Only bottles, not preforms, are inspected by the BNF module. Proper synchronization of the BNF module with respect to the position of a bottle to be inspected is preferably triggered by a sensor ring responsive to a sprocket or gear coupled to the rotational drive of one or both of transfer arms 60, 20, e.g., having a plurality of capacitive proximity detectors which sense when the container is in the proper position as discussed below. Alternatively the BNF module can be triggered by a lamp/photocell pair (not shown) whose beam path is broken by the container or by the transfer arm. Alternatively, other angle encoding means such as limit switches or the like can synchronize image collection to the position of the transfer arm and the container therein. An image is collected when each passing container is in position clear of the passing preform.

Returning to FIG. 15, lower module 52 is coupled to the base plate 300 between the two transfer arms. The upper module 54 is mounted above the lower module by means not shown. The upper module is mounted such that the camera 270 is directly above the second light source 210 located in the center yoke section 140 of the lower module. Light from the second light source travels in the upward direction coincident with the line of sight 275. Accordingly, the BNF inspection head is basically mounted to encompass the passing bottles and preforms without interfering in any respect with the transport of the bottles or preforms. Whereas the second transfer arm extracts bottles from the molding apparatus and holds the bottles while carrying them along, each bottle is presented in the same orientation to the inspection system.

FIG. 13 shows a view of the finish gauge inspection (FGI) module with the front cover removed. Finish Gauge inspection module has a U-shaped chassis 280 with a first and second leg 290, 310, which extend downward, joined by a center yoke section 320.

The first leg 290 has an opening, through which light can pass, covered by a clear glass panel 330, a first mirror 340 and a camera 350 positioned to receive an image that is reflected via first mirror 340. First mirror 340 is set at a 45° so that the camera receives an image from the area between the two legs 290, 310 along the line of sight 355 as shown by dotted lines.

The second leg has an opening through which light can pass along the line of sight 355. A light source 360 is aimed at a second mirror 370 such that light from the light source strikes the second mirror and travels along the line of sight 355. As in the above embodiments, a diffuse panel can be employed to provide even backlighting on the illumination side, and on the viewing side any covering panel is clear. Air curtain means (not shown) can be provided to reduce the buildup of dust on either or both sides.

The position line of sight is oriented such that when a bottle is placed between the two legs, the line of sight passes through the bottle or is reflected by the bottle, providing outline contrast that can be analyzed using edge-emphasizing image processing routines. The image features are also characterized by contrast due to variations in the surface configuration of the bottle due either to topographical features such as threads or defects in the otherwise substantially clear PET/PEN material.

The SSI and BNF modules as discussed above, provide a plan view of the sealing edge and substantially axial and transverse views of the bottle. Insofar as a further outline view of the bottle is also useful for accept/reject decisions, a finish gauge inspection (FGI) module can be employed. In FIG. 1, the SSI and BNF modules are located in the area of second transfer arm 60, where the rotational orientation of the bottles is known dependably as they have just exited blow molder 30. Therefore, measurements taken of rotationally positioned features such as the told in the bottom of a petaloid PET/PEN bottle are advantageously collected here. The finish gauge inspection module 70, as shown in FIG. 1, can be used for measurements that are not rotationally specific, such as the outside diameter of the bottles above the folds of the base, the overall height and the like. Although the orientation of the bottles is substantially constant due to the repeatable action of the engaging mechanisms of the second transfer arm 60 and exit star wheel 90, measurements sensitive to bottle rotational angle are best made upstream along the conveying path. The FGI module can have a structure comparable to that of the BNF module, but is dimensioned and positioned to collect an image having the desired span. The exit star wheel 90 holds the bottles by the body, as opposed to the individual arm members of the first and second transfer arms which grasp the bottle about the neck area. The FGI is advantageously positioned at the exit star wheel so that the neck area of the bottle is not obstructed by the individual arm members.

Proper synchronization of the FGI module with respect to the position of a bottle to be inspected is preferably triggered by a sensor ring having a plurality of capacitive proximity detectors which sense when the container is in the proper position as discussed below. Alternatively the BNF module can be triggered by a lamp/photocell pair (not shown) whose beam path is broken by the container or by the exit star wheel. Alternatively, other angle encoding means such as limit switches or the like can synchronize image collection to the position of the transfer arm and the container therein.

The respective frames collected by the SSI, BNF and FGI are associated by a control processor (not shown) with the same bottle, which requires that either the images be stored for several bottles or that the processing results for particular images (especially their accept/reject results as compared to stored criteria) be stored as the bottles advance. Diverter mechanism 45 is operated or not operated to discriminate selected bottles from rejected ones, based on the accept/reject results from the SSI and/or BNF only. Diverter mechanism 80 is operated or not operated to discriminate selected bottles from rejected ones, based on the accept/reject results from the SSI, BNI and FGI or any combination thereof.

The images can be analyzed separately for the data in individual images, or the controller can have stored criteria that encompass more than one of the images, depending on the specific selection/rejection characteristics that are desired. Thus, for example, the criteria can potentially allow for a strict criteria for the sealing surface smoothness, and variable criteria for certain BNF and FGI characteristics, whereby the criteria for one or both of BNF and FGI acceptance or rejection are based on the extent to which the criteria of the other are met. If a given bottle has a low total score considering BNF and FGI results together, the bottle is rejected; whereas the criteria may be more forgiving for BNF or FGI if the results of the other are good. As another possibility, it will often be appropriate to impose strict criteria to potential defects that are functionally important, such as the continuity of threads (e.g., see U.S. Pat. No. 4,914,289-Nguyen et al.), whereas other criteria such as the clarity of the plastic of a sidewall may be less important in that they are cosmetic rather than functionally critical. It will be appreciated that various other possibilities for selection criteria are also possible.

Image processing apparatus comprising frame grabbers and parallel processing circuits for analyzing image data are known and can be used in connection with the inspection system of the invention. For example, appropriate image processors are available frown companies such as Imaging Technology Inc., Woburn Mass. that are operable with triggerable video cameras operable to collect a freeze frame image for analysis, available for example from Hitachi Denshi, Ltd., Woodbury, N.Y. Other similar image inspection processors are also known and can be applied to the apparatus of the invention as discussed above.

The SIDEL® SBO 24/24 has a heat conditioning wheel for heating preforms with 186 spindles. There are 24 individually controllable heating units which heat preforms to a softening temperature in preparation for blow molding. The blow molder has 24 cavities, each of which is individually cooled with chilled water and operable to form a bottle. As shown in FIG. 14 first and second transfer arms each have 12 individual arm members.

Due to the serial nature of the production path of the SIDEL® SBO 24/24, a bottle formed in a particular cavity will have been associated with a particular spindle, heated by a corresponding heating unit and transferred by corresponding arm members of the first and second transfer arms. For illustration purposes only, assume each of the spindles are numbered 1 through 186, each of the heating units number 1 though 24, each of the cavities numbered 1 through 24, and each of the arm members numbered 1 through 12. A preform located on spindle 1 is heated by heating unit 1 and then transferred by first transfer arm member 1 to cavity 1 where a bottle is formed; the bottle is then transferred from cavity 1 by second transfer arm member 1. The relationship between the spindles, heating units, cavities and transfer arm members is shown in Tables 1 and 2 below.

TABLE 1

| SPINDLE # | HEATING # | FIRST TRANSFER ARM # | CAVITY # | SECOND TRANSFER ARM # |
|---|---|---|---|---|
| 1 | 1 | 1 | 1 | 1 |
| 2 | 2 | 2 | 2 | 2 |
| 3 | 3 | 3 | 3 | 3 |
| 4 | 4 | 4 | 4 | 4 |
| 5 | 5 | 5 | 5 | 5 |
| 6 | 6 | 6 | 6 | 6 |
| 7 | 7 | 7 | 7 | 7 |
| 8 | 8 | 8 | 8 | 8 |
| 9 | 9 | 9 | 9 | 9 |
| 10 | 10 | 10 | 10 | 10 |
| 11 | 11 | 11 | 11 | 11 |
| 12 | 12 | 12 | 12 | 12 |
| 13 | 13 | 1 | 13 | 1 |
| 14 | 14 | 2 | 14 | 2 |
| 15 | 15 | 3 | 15 | 3 |
| 16 | 16 | 4 | 16 | 4 |
| 17 | 17 | 5 | 17 | 5 |
| 18 | 18 | 6 | 18 | 6 |
| 19 | 19 | 7 | 19 | 7 |
| 20 | 20 | 8 | 20 | 8 |
| 21 | 21 | 9 | 21 | 9 |
| 22 | 22 | 10 | 22 | 10 |
| 23 | 23 | 11 | 23 | 11 |
| 24 | 24 | 12 | 24 | 12 |

TABLE 2

| HEAT CONDITIONING WHEEL REVOLUTION # | TRANSFER ARM #s | SPINDLE #s | HEATING UNIT #s |
|---|---|---|---|
| 1 | 1–12 | 1–12 | 1–12 |
| 1 | 1–12 | 13–24 | 13–24 |
| 1 | 1–12 | 25–36 | 1–12 |
| . | . | . | . |
| . | . | . | . |
| 1 | 1–12 | 169–180 | 1–12 |
| 1 | 1–6 | 181–186 | 13–18 |
| 2 | 7–12 | 1–6 | 19–24 |
| 2 | 1–12 | 7–18 | 1–12 |
| 2 | 1–12 | 19–30 | 13–24 |
| . | . | . | . |
| 2 | 1–12 | 163–174 | 13–24 |
| 2 | 1–12 | 175–186 | 1–12 |
| 3 | 1–12 | 1–12 | 13–24 |
| 3 | 1–12 | 13–24 | 1–12 |
| . | . | . | . |

TABLE 2-continued

| HEAT CONDITIONING WHEEL REVOLUTION # | TRANSFER ARM #s | SPINDLE #s | HEATING UNIT #s |
|---|---|---|---|
| 3 | 1–12 | 169–180 | 12–24 |
| 3 | 1–6 | 181–186 | 1–6 |
| 4 | 7–12 | 1–6 | 7–12 |
| 4 | 1–12 | 7–18 | 13–24 |
| . | . | . | . |
| . | . | . | . |
| . | . | . | . |
| 4 | 1–12 | 163–174 | 1–12 |
| 4 | 12–24 | 175–186 | 13–24 |
| 5 | 1–12 | 1–12 | 1–12 |
| . | . | . | . |
| . | . | . | . |
| . | . | . | . |

Thus, according to this embodiment, the relationship of the respective elements is known and can be correlated. The processor must cross reference the relationship between the spindles and the other elements (i.e., heating units, cavities, transfer arms). This relationship is not constant but is known. The phase relationship of the spindles with respect to the other elements changes with each revolution of the heat conditioning wheel. A phased relationship occurs because there are 186 spindles and 186 is not evenly divisible by 12. Table 2 shows how the various spindles map to particular transfer arms and heating units. The relationship between spindles and transfer arms alternates upon every other rotation of the heat conditioning wheel. The relationship between spindles and heating units arms repeats every fourth rotation of the of the heat conditioning wheel.

As shown in Table 1, bottles heated by heating units 1 through 12 are transferred by arm members 1 through 12. Bottles heated by heating units 13 through 24 are also transferred by arm members 1 through 12. It will take two complete revolutions of the transfer arms to service all 24 heating elements. As shown in Table 2, preforms located on spindles 1–12 are heated by heating units 1–12 and are transferred by transfer arms 1–12. Preforms located on spindles 12–24 are heated by heating units 12–24 and are also transferred by transfer arm numbers 1–12. As shown in Table 2, it will take four complete revolutions of the heat conditioning wheel before preforms located on spindles 1–12 are again heated by heating units 1–12 and transferred by transfer arms 1–12.

As discussed above, the processor is operable to store data collected by SSI, BNF and FGI modules concerning defective bottles. The processor is also operable to correlate the defects to a particular spindle and/or heating unit and/or cavity, knowing that the defective bottle was transferred by a particular arm member. If there are defects detected in bottles transferred by a particular transfer arm, the processor can determine that the defect necessarily correlates to problems with specific spindles, cavities and heating, knowing the relationships shown in Tables 1 and 2.

Defects associated with a particular element in the manufacturing process will occur on a periodic basis. Defects associated with a particular transfer arm member will occur every 12 bottles. Defects associated with a particular cavity or heating unit will occur every 24 bottles. Defects associated with a particular spindle will occur every 186 bottles. The processor is operable to correlate the information in Tables 1 and 2 and the frequency of a periodic defect to identify and report the most likely causes of the defect.

In addition to synchronization as a matter of counting, the inspection heads can vary in phase relationship to the precise position of the elements. Preferably, the respective inspection heads are mounted using a mounting plate arrangement that engages the cabinet of the inspection head for precisely fixing the position of the inspection head, for example as shown in FIGS. 8–12. The mounting plate is permanently bolted into position. Should it be necessary to remove an inspection head for maintenance, the mounting plate and the locating pins thereon ensure that the cabinet of the inspection head will be returned to the same position when attached again to the mounting plate.

Figure 17:
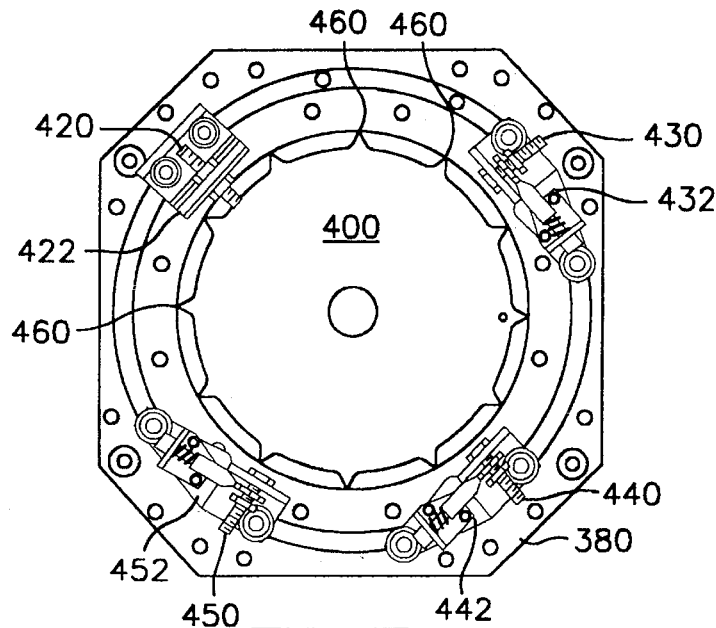
FIG. 17 is a top view of a synchronizing sensor ring and sprocket in accordance with the invention.
Figure 19:
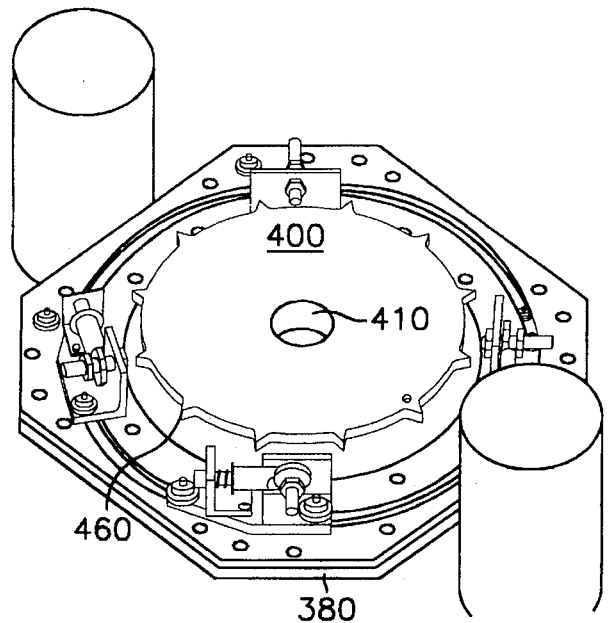
FIG. 19 is an isometric view of sensor ring and sprocket.

As a setup procedure, the triggering signals for the respective inspection heads are precisely adjustable in phase relative to the operation of the molding machine, and more specifically the transfer arms. A sensor ring as shown in FIG. 17 has a mounting plate 380 and four sensors 420, 430, 440, 450 disposed in ring-like fashion about the periphery of the mounting plate. A sprocket 400 formed with a hub 410 (FIG. 19) is located such that the periphery of the sprocket equidistant from the four sensors. The hub 410 is engaged coaxially with the axle which drives the transfer arms such that the sprocket can rotate relative to the base plate 380. The sprocket can be formed with a number of teeth 460 (e.g., twelve) corresponding to the number of arm positions. The teeth 460 are equally spaced about the periphery of the sprocket.

Figure 18:
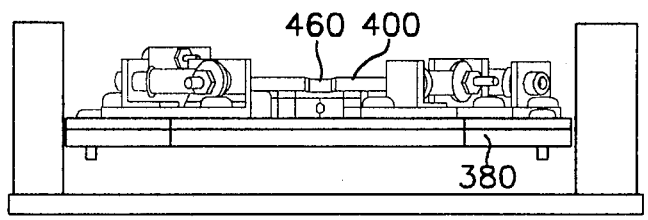
FIG. 18 is a front view of the sensor ring and sprocket.

FIGS. 14 and 18 shows the mounting location for the sensor ring with respect to the transfer arms. FIG. 14 shows only the sprocket 400, and not the mounting plate 380, for clarity. Various methods can be used to secure the sensor ring to the transfer arms such as screws or bolts (not shown). The hub 410 is positioned such that the hub and the axles 24, 64 share the same axis of rotation. Each one of the twelve teeth 460 are mechanically associated with an individual arm member and interact with sensors to provide phase position information.

Sensors 420, 430, 440 and 450 are preferably capacitive proximity detectors which can accurately detect the position of the teeth 460 without physically touching the teeth. Other means of sensing the position of the sprocket such as a inductive or magnetic pickups, mechanical push switches which are depressed by the teeth, or a lamp/photocell pair whose beam path is broken by the teeth can alternatively be used. The sensors are mounted to adjustors 422, 432, 442 and 452 such that the position of the sensors with respect to the sprocket may be precisely adjusted to provide the appropriate triggering signals for collection of video frames by the inspection heads, operation of the reject mechanism, etc.

The output of the sensors can be coupled to the processor such that the processor is operable to synchronize the image processing apparatus contained within the SSI, BNF and FGI modules with respect to the transfer arms and diverter mechanisms (or reject arms). Alternatively, the video cameras in the inspection heads can be triggered directly from the sensor signals.

Figure 20:
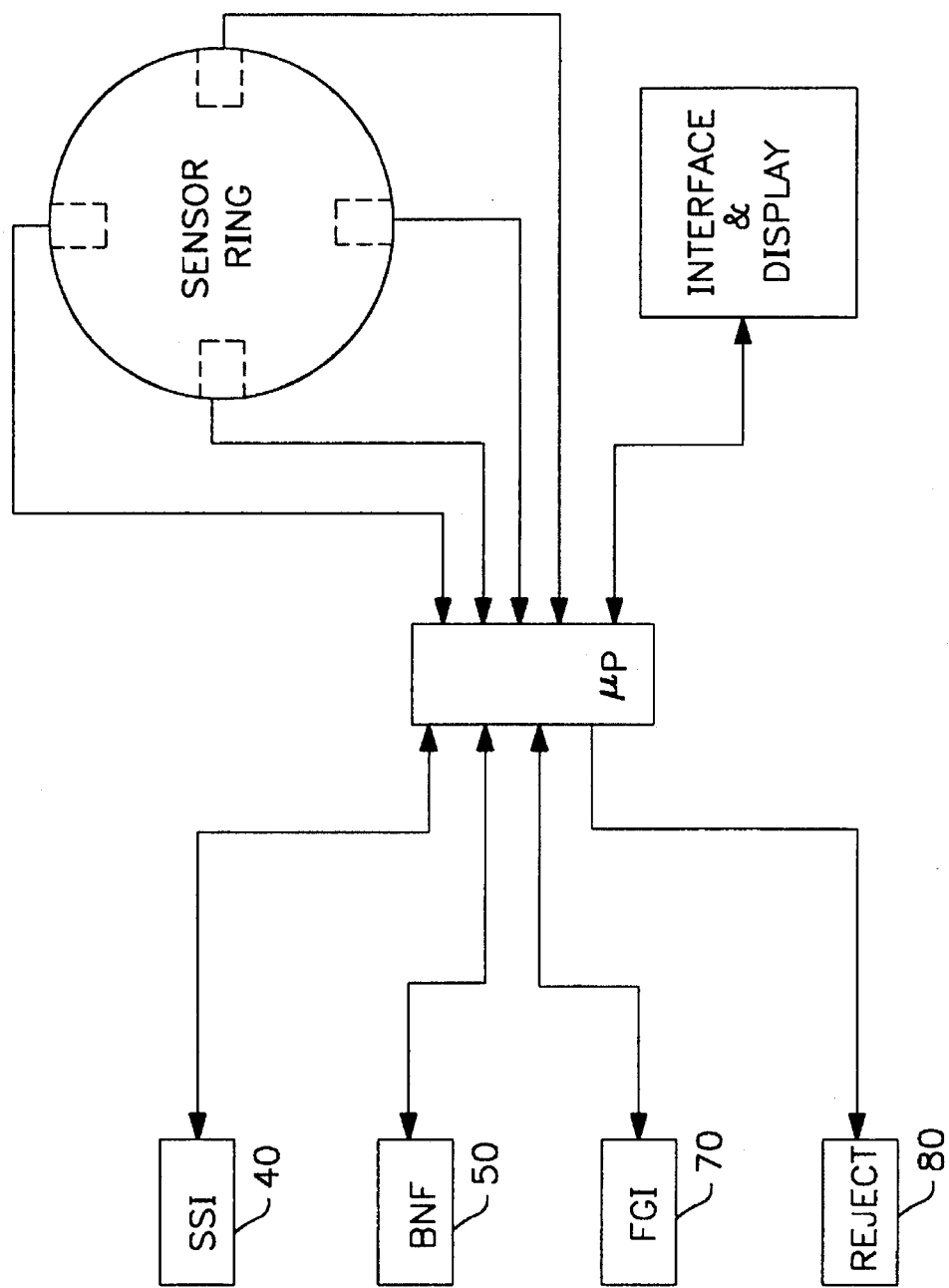
FIG. 20 is a functional block diagram illustrating the signal interconnections provided according to the invention.

A functional block diagram illustrating the signal interconnections provided according to the invention is shown in FIG. 20. The sensor ring provides phase and triggering information; the inspection heads provide video data; and the processor manages operation of the reject mechanism (either directly or by providing a triggering signal to an existing reject mechanism) and reports to the operator interface (e.g., a display, printer or the like) data such as the statistical performance of the individual mold heads and/or transfer mechanisms.

Alternatively a rotary encoder can be mounted to a transfer arm axle or other suitable rotating shaft suitable to provide similar triggering information.

The invention having been described with respect to particular embodiments considered exemplary, variations comporting with the invention will now be apparent to persons skilled in the art. The invention is not limited to the precise arrangements disclosed as examples. Accordingly, reference should be made to the appended claims rather than the foregoing Specification, to assess the scope of exclusive rights in the invention claimed.

What is claimed is:

1. A container inspection system in combination with a container manufacturing system, comprising:

a molder formed with at least one cavity, the molder being coupled to a preform feed means and having at least one cavity for receiving a succession of preforms and to form the preforms to a shape of the cavity, the molder forming a container with a top seal means on a neck formed with an opening, and a base;

a transfer means positioned after the blow molder along a transport path, and being operable to remove each container from the cavity and to transport the container along the transport path toward an exit means, the transfer means maintaining a predetermined rotational position of each container received from the molder;

at least one optical inspection device disposed along the transport path between the molder and the exit means, the transfer means presenting the container to the inspection system at said predetermined rotational position for each successive container, the at least one optical inspection device being operable to capture an image of at least part of the container and being coupled to a processor for analyzing the image for defects in the container;

at least one of an additional optical inspection device and a rejection means coupled along the transport path, and being coupled to the processor, the processor having means coupled to the transport path for coordinating operation of the at least one optical inspection device and said processor correlating operation of at least one of the optical inspection device, the additional optical inspection device and the rejection means, as to individual ones of the containers, whereby defective operation of the cavity of the molder and the transfer means can be identified.

2. The combination of claim 1, wherein the molder is a blow molder and the cavity is circularly asymmetric so as to form the container with a shape having a distinct appearance at different rotational positions.

3. The combination of claim 2, wherein the molder forms bottles having folds in a base thereof, the folds being disposed at particular angles relative to the predetermined rotational position of the containers.

4. The combination of claim 2, wherein the molder is a blow molder operable to form petaloid polyethylene terephthalate bottles having folds in a base thereof, formed by the cavity.

5. The combination of claim 4, wherein the inspection system comprises a base/neck fold module operable to record an image including the folds.

6. The combination of claim 5, further comprising said additional optical inspection device, including at least one of a seal surface inspection module and a finish gauge module, each operable to record an image of the container independent of rotational position of the container.

7. The combination of claim 6, wherein the finish gauge inspection module comprises a U-shaped chassis having two downward extending legs joined by a center yoke section, a first light source, at least one reflecting mirror and a camera, the light source being positioned to illuminate an area between the downward extending legs of the U-shaped chassis, the camera being positioned to image the bottle when the bottle is positioned within the area between the downward extending legs of the U-shaped chassis while the bottle is being transported along the transport path.

8. The combination of claim 5, wherein the base/neck fold inspection module further comprises an upper module operable to inspect the base of the bottle and a lower module operable to inspect the neck area of the bottle while the bottle is being transported along the transport path.

9. The combination of claim 8, wherein the lower module comprises a U-shaped chassis having two upward extending legs joined by a center yoke section, the lower module having a first light source, at least one reflecting mirror and a camera, the first light source being positioned to illuminate the area between the upward extending legs of the U-shaped chassis, the camera being positioned to image the bottle when the bottle is positioned within the area between the upward extending legs of the U-shaped chassis.

10. The combination of claim 8, wherein the lower module further comprises a second light source positioned in the center yoke section operable to direct light in the upward direction parallel to the direction of the upward extending legs.

11. The combination of claim 10, wherein the upper module comprises a rectangular chassis and a camera.

12. The combination of claim 11, wherein the upper module is located above the lower module such that upper module camera is directed at the second light source in the lower module, the upper module camera being operable to image the base of the bottle by viewing the base through the opening in the neck when the bottle is positioned below the camera and above the second light source.

13. The combination of claim 1, further comprising an operator interface system having a processing means in data communication with the at least one optical inspection device, the processing means being operable to analyze for defects in the container that are detected by said inspection device and to actuate the rejection means such that a defective container is diverted along the transport path.

14. The combination of claim 13, further comprising means for triggering the optical inspection device to record the image at the predetermined rotational position of the container.

15. A container inspection system in combination with a container manufacturing system, comprising:

a molding means having a plurality of cavities, the molding means being operable to form a container defined by the shape of the plurality of cavities, the container having a top seal means on a neck formed with an opening, and a base;

a transfer means having a plurality of transfer arms being positioned after the molding means along a transport path, and being operable to remove each container from the cavity and to transport the container along the transport path toward an exit means, the transfer means maintaining a predetermined rotational position of each container received from the molding means;

an optical inspection system disposed along the transport path between the molding means and the exit means, the transfer means presenting the container to the optical inspection system at said predetermined rotational position for each successive container, the optical inspection system being operable to capture an image of at least part of the container and being coupled to a processor for analyzing the image for defects in the container, the processor being operable to correlate defects detected in the container to the cavity in which the container was formed; and, a rejection means coupled along the transport path, and being responsive to the processor for diverting selected ones of the containers as a function of the defects.

16. The container inspection system of claim 15 wherein the processor is operable to correlate defects detected in the container to the transfer arm which removed the container from the cavity.

17. The container inspection system of claim 16 wherein the processor is operable to store defect data for each of the plurality of cavities and transfer arms.

18. The container inspection system of claim 17 wherein the processor is operable to display the defect data on a display screen.

19. The container inspection system of claim 18 wherein the processor is operable to display the detect in the form of a histogram.

20. A container inspection system in combination with a container manufacturing system, comprising:

molding means operable to form a container from a heated preform, the container having a top seal means on a neck formed with an opening, and a base;

transfer means positioned after the molding means along a transport path, and being operable to move containers away from molding means along the transport path toward an exit means, at least one of the molding means and the transfer means having a plurality of container engaging elements such that successive ones of the containers are engaged by different ones of the container engaging elements;

an optical inspection system disposed along the transport path between the molding means and the exit means, the optical inspection system being operable to capture an image of at least part of the container and being coupled to a processor for analyzing the image for defects in the container, the processor being operable to correlate defects detected in the container to particular ones of said container engaging elements.

21. The combination of claim 20, wherein the inspection system comprises a base/neck fold module disposed adjacent to the transfer means, the base/neck fold module being operable to record an image of the base and neck of the container.

22. The combination of claim 21, further comprising at least one of a seal surface inspection module disposed adjacent to the transfer means, the seal surface inspection module being operable to record an image of the seal surface of the container.

23. The combination of claim 22, further comprising an operator interface system having a processing means in data communication with the optical inspection system, the processing means being operable to analyze for defects in the container that are detected by the optical inspection system and to actuate the rejection means such that a defective container is diverted along the transport path.

24. The combination of claim 23, further comprising means for triggering the optical inspection system to record the image at the predetermined rotational position of the container.

25. The combination of claim 21, wherein the base/neck fold inspection module further comprises an upper module operable to inspect the base of the bottle and a lower module operable to inspect the neck area of the bottle while the bottle is being transported along the transport path.

26. The combination of claim 25, wherein the lower module comprises a U-shaped chassis having two upward extending legs joined by a center yoke section, the lower module having a first light source, at least one reflecting mirror and a camera, the first light source being positioned to illuminate the area between the upward extending legs of the U-shaped chassis, the camera being positioned to image the bottle when the bottle is positioned within the area between the upward extending legs of the U-shaped chassis.

27. The combination of claim 26 wherein the lower module further comprises a second light source positioned in the center yoke section operable to direct light in the upward direction parallel to the direction of the upward extending legs.

28. The combination of claim 27, wherein the upper module comprises a rectangular chassis and a camera.

29. The combination of claim 28, wherein the upper module is located above the lower module such that the upper module camera is directed at the second light source in the lower module, the upper module camera being operable to image the base of the bottle by viewing the base through the opening in the neck when the bottle is positioned below the camera and above the second light source.

30. The combination of claim 22, wherein the exit means is an exit star wheel operable to hold the container about the body such that the neck area is unobstructed.

31. The combination of claim 30, further comprising at least one final gauge module disposed adjacent to the exit star wheel, the final gauge module being operable to record an image of the container including the neck area.

32. The combination of claim 31, wherein the finish gauge module comprises a U-shaped chassis having two downward extending legs joined by a center yoke section, a first light source, at least one reflecting mirror and a camera, the light source being positioned to illuminate an area between the downward extending legs of the U-shaped chassis, the camera being positioned to image the bottle when the bottle is positioned within the area between the downward extending legs of the U-shaped chassis while the bottle is being transported along the transport path.

* * * * *